(12) United States Patent
Miller et al.

(10) Patent No.: US 11,591,108 B2
(45) Date of Patent: *Feb. 28, 2023

(54) COMBINED AUTOMATIC DEPENDENT SURVEILLANCE-BROADCAST AND CARBON MONOXIDE DETECTING DEVICE

(71) Applicant: The Boeing Company, Chicago, IL (US)

(72) Inventors: Jason Miller, Austin, TX (US); Paul Beard, Bigfork, MT (US); Jeffrey Walker, Republic, MO (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/511,339

(22) Filed: Oct. 26, 2021

(65) Prior Publication Data
US 2022/0048642 A1 Feb. 17, 2022

Related U.S. Application Data

(62) Division of application No. 16/503,212, filed on Jul. 3, 2019, now Pat. No. 11,203,442.

(51) Int. Cl.
| | |
|---|---|
| *B64D 45/00* | (2006.01) |
| *H04W 4/42* | (2018.01) |
| *G08G 5/00* | (2006.01) |
| *G01N 33/00* | (2006.01) |
| *G01S 13/76* | (2006.01) |
| *G01S 13/933* | (2020.01) |

(52) U.S. Cl.
CPC .......... *B64D 45/00* (2013.01); *G01N 33/007* (2013.01); *G01N 33/0063* (2013.01); *G01S 13/765* (2013.01); *G01S 13/933* (2020.01); *G08G 5/0021* (2013.01); *H04W 4/42* (2018.02)

(58) Field of Classification Search
CPC ........ B64D 45/00; B64D 13/00; B64D 43/00; G01N 33/0063; G01N 33/007; G01S 13/765; G01S 13/933; G01S 13/781; G08G 5/0021; G08G 5/0008; G08G 5/0013; G08G 5/0078; G08G 5/0091; H04W 4/42

See application file for complete search history.

(56) References Cited

U.S. PATENT DOCUMENTS

| | | |
|---|---|---|
| 5,276,434 A | 1/1994 | Brooks et al. |
| 6,448,888 B1 | 9/2002 | Horner et al. |
| 6,456,911 B1 | 9/2002 | Muramatsu |
| 8,751,242 B2 | 6/2014 | Arasada |
| 9,513,376 B1 | 12/2016 | Heinrich et al. |
| 10,094,667 B2 | 10/2018 | Das Adhikary |

(Continued)

*Primary Examiner* — Ojiako K Nwugo
(74) *Attorney, Agent, or Firm* — Ferguson Braswell Fraser Kubasta PC

(57) ABSTRACT

An in-flight safety enhancing system including: a combined automatic dependent surveillance broadcast (ADS-B) and carbon monoxide (CO) detecting device configured to receive an ADS-B transmission and obtain a CO reading; and a flight application executing on an aircraft crew computing device separate from the combined ADS-B and CO detecting device, and configured to: receive the ADS-B transmission and the CO reading; augment the flight application with information extracted from the ADS-B transmission; and provide a CO status notification when the CO reading exceeds a CO threshold value.

20 Claims, 9 Drawing Sheets

(56) References Cited

U.S. PATENT DOCUMENTS

| | | | |
|---|---|---|---|
| 10,302,759 B1 | 5/2019 | Arteaga | |
| 2003/0048203 A1 | 3/2003 | Clary et al. | |
| 2015/0194059 A1 | 7/2015 | Starr et al. | |
| 2016/0176538 A1 | 6/2016 | Bekanich | |
| 2017/0005401 A1 | 1/2017 | Duchesne et al. | |
| 2017/0193789 A1 | 7/2017 | Economy et al. | |
| 2017/0324437 A1* | 11/2017 | Ruttler | A61B 5/145 |
| 2018/0182250 A1 | 6/2018 | Bonnet et al. | |
| 2019/0033862 A1 | 1/2019 | Groden et al. | |
| 2019/0355264 A1 | 11/2019 | Dolan et al. | |
| 2019/0362638 A1 | 11/2019 | Donhoffner et al. | |

* cited by examiner

COMBINED AUTOMATIC DEPENDENT SURVEILLANCE-BROADCAST AND CARBON MONOXIDE DETECTING DEVICE

RELATED APPLICATIONS

This application is a divisional application of U.S. patent application Ser. No. 16/503,212, filed Jul. 3, 2019, the entirety of which is hereby incorporated by reference.

BACKGROUND

Aircraft are increasingly equipped with surveillance technology such as the automatic dependent surveillance-broadcast (ADS-B) technology, providing the aircraft crew with weather, traffic, and other information. ADS-B equipment helps lower an aircraft crew's workload, increases safety, and may become mandatory in the future.

SUMMARY

In general, in one aspect, one or more embodiments relate to an in-flight safety enhancing system comprising: a combined automatic dependent surveillance broadcast (ADS-B) and carbon monoxide (CO) detecting device configured to receive an ADS-B transmission and obtain a CO reading; and a flight application executing on an aircraft crew computing device separate from the combined ADS-B and CO detecting device, and configured to: receive the ADS-B transmission and the CO reading; augment the flight application with information extracted from the ADS-B transmission; and provide a CO status notification when the CO reading exceeds a CO threshold value.

In general, in one aspect, one or more embodiments relate to a method for enhancing in-flight safety, the method comprising: obtaining, by a combined ADS-B and CO detecting device, a CO reading from a CO sensor; receiving, by the combined ADS-B and CO detecting device, an ADS-B transmission; and integrating, by the combined ADS-B and CO detecting device, the CO reading and the ADS-B transmission into a data stream; and transmitting, by the combined ADS-B and CO detecting device, the data stream to an aircraft crew computing device.

Other aspects of the disclosed disclosure will be apparent from the following description and the appended claims.

DETAILED DESCRIPTION

Figure 1:
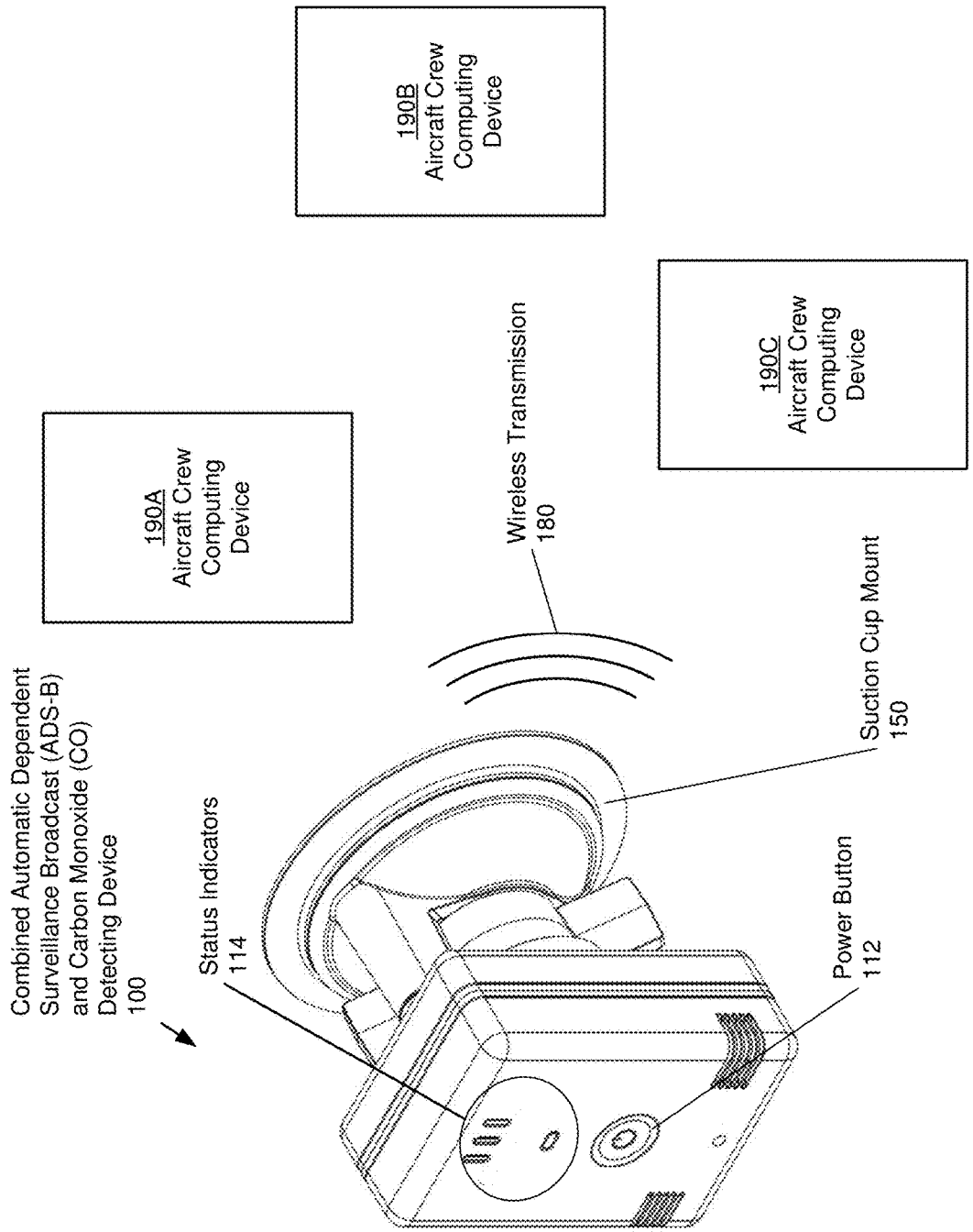
FIG. 1 shows a combined automatic dependent surveillance broadcast (ADS-B) and carbon monoxide (CO) detecting device communicating with aircraft crew computing devices, in accordance with one or more embodiments of the disclosure.

Specific embodiments of the disclosed technology will now be described in detail with reference to the accompanying figures. Like elements in the various figures may be denoted by like reference numerals and/or like names for consistency.

The following detailed description is merely exemplary in nature, and is not intended to limit the disclosed technology or the application and uses of the disclosed technology. Furthermore, there is no intention to be bound by any expressed or implied theory presented in the preceding technical field, background, brief summary or the following detailed description.

In the following detailed description of embodiments of the disclosed technology, numerous specific details are set forth in order to provide a more thorough understanding of the disclosed technology. However, it will be apparent to one of ordinary skill in the art that the disclosed technology may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Various embodiments of the disclosure enable a combined automatic dependent surveillance broadcast (ADS-B) and carbon monoxide (CO) detecting device, in accordance with one or more embodiments. The combination of an ADS-B device and a CO detecting device may provide additional safety to flight crews. The ADS-B component may provide weather, traffic and other information services to the flight crew. These services may improve the flight crew's ability to make informed decisions, reduce the workload, improve situational awareness, etc. The CO detecting component may warn the flight crew of potentially dangerous CO levels inside the cabin.

The combined automatic dependent surveillance broadcast (ADS-B) and CO detecting device in a portable configuration may be particularly suitable for use in smaller aircraft that are not necessarily equipped with a permanently installed ADS-B system. Similarly, the availability of the CO sensor may be highly beneficial in smaller aircraft where CO ingress may occur when cabin heating is obtained by directing fresh air over the engine muffler, allowing CO-rich exhaust gases to enter the cabin in case of a leaky exhaust system.

Turning to FIG. 1, a combined ADS-B and CO detecting device (100) communicating with aircraft crew computing devices (190A-190C), in accordance with one or more embodiments of the disclosure, is shown. The ADS-B and CO detecting device (100) and the aircraft crew computing devices (190A-190C) may communicate via wireless transmissions (180).

In one or more embodiments, the combined ADS-B and CO detecting device (100) is portable and may be temporarily installed in an aircraft. A suction cup mount (150) may be used to removably mount the combined ADS-B and CO detecting device (100) to a surface inside an aircraft cabin such as the windshield of the aircraft. The combined ADS-B and CO detecting device (100) may be integrated in a single compact housing to avoid blocking the view of the pilot. In one or more embodiments, the combined ADS-B and CO detecting device (100) includes a power button (112) and status indicators (114), whose functions are described below.

Features provided by the combined ADS-B and CO detecting device (100) may be used by the pilot of the aircraft, the copilot of the aircraft, and/or passengers of the aircraft. The features may be made available on the aircraft crew computing devices (190A-190C), which may be tablets, smartphones, laptop computers, etc., that are wirelessly connected to the combined ADS-B and CO detecting device (100). The ADS-B and CO detecting device (100) in combination with one or more aircraft crew computing devices (190A-190C) may form an in-flight safety enhancing system. A detailed description of the features of the combined ADS-B and CO detecting device (100) is provided below.

Figure 2:
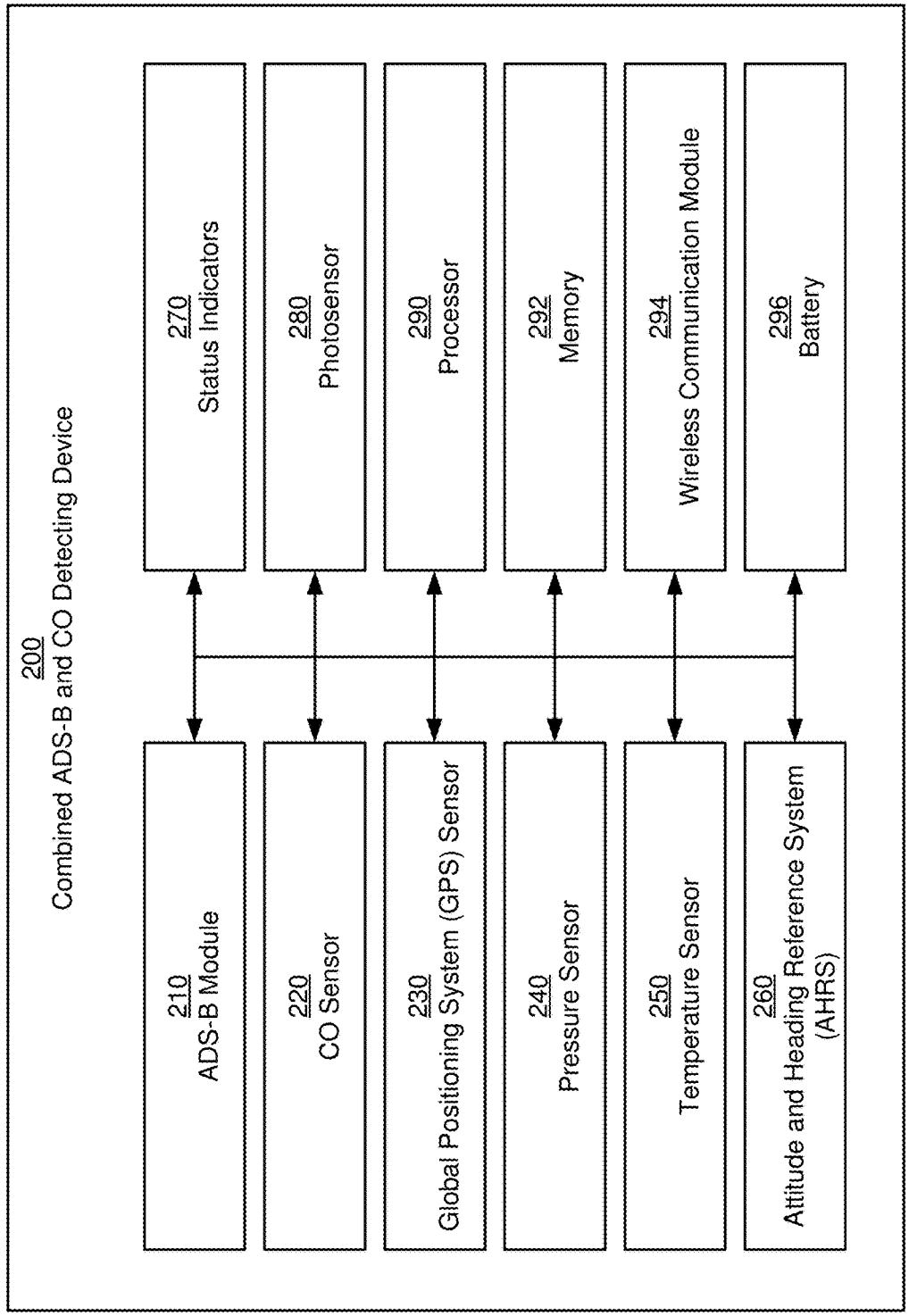
FIG. 2 shows a block diagram of a combined ADS-B and CO detecting device, in accordance with one or more embodiments of the disclosure.

Turning to FIG. 2, a block diagram of a combined ADS-B and CO detecting device (200), in accordance with one or more embodiments of the disclosure, is shown. The combined ADS-B and CO detecting device (200) includes an ADS-B module (210), a CO sensor (220), a GPS sensor (230), a pressure sensor (240), a temperature sensor (250), and/or an attitude and heading reference system (AHRS) (260). Further, the combined ADS-B and CO detecting device (200) may include status indicators (270), a photosensor (280), a processor (290), a memory (292), a wireless communication module (294), and a battery (296). Each of these components is subsequently described.

The ADS-B module (210) may provide inflight weather traffic and other information to users of the combined ADS-B and CO detecting device (200). Broadly speaking, the ADS-B module receives ADS-B transmissions. More specifically, weather and other information such as notices to airmen (NOTAMs) may be obtained using the Flight Information System Broadcast (FIS-B) service. Further, traffic may be obtained using the Traffic Information System Broadcast (TIS-B) service. In one or more embodiments, the ADS-B module (210) operates in the ADS-B In mode. The signals for the FIS-B and/or TIS-B services may be received from ground towers and/or air-to-air. The ADS-B module is an ADS-B circuitry that may include antennas, signal processing circuitry, processors, and a communication interface to output the received information to the processor (290). In one or more embodiments, an extended GDL90 protocol is used for the communications of the between ADS-B device.

The CO sensor (220) may provide CO measurements of the ambient air, e.g., in the aircraft cabin. The CO sensor may be a semiconductor-based sensor, such as a metal oxide semiconductor sensor. Any CO sensing principle may be used without departing from the disclosure. The output of the CO sensor may be processed by a signal conditioning circuit of the CO sensor. The processing may include amplification and analog to digital conversion. The processed output of the CO sensor may be received by the processor (290) as a CO reading. The CO sensor may perform a periodic self-test to ensure proper operation. A CO sensor status signal may be provided to the processor (290) to indicate whether the CO sensor is operating properly.

The GPS sensor (230) may provide location information. The location information may be available to the aircraft crew computing devices and may be used, for example, to update the current location in a displayed map, which may then be used for other functionalities such as traffic display functions, including the filtering of distant traffic and traffic alerting. In addition, a current time obtained from the GPS sensor (230) may be used by the combined ADS-B and CO detecting device (100) to maintain an internal time, which may be used for logging events, etc. The GPS sensor may support various Global Navigation Satellite Systems (GNSS) such as GPS including Wide Area Augmentation System (WAAS), Galileo, GLONASS, and BeiDu. The GPS sensor (230) may digitally interface with the processor (290) to provide the location information.

The pressure sensor (240) may provide pressure measurements that may be used to determine an altitude. The pressure sensor may be based on any sensing principle, without departing from the disclosure. The output of the pressure sensor may be processed by a signal conditioning circuit of the pressure sensor. The processing may include amplification and analog to digital conversion. The processed output of the pressure sensor may be received by the processor (290).

The temperature sensor (250) may provide temperature measurements. The temperature sensor may be a thermocouple or a resistive-type temperature sensor. Alternatively, any other temperature sensing principle may be used without departing from the disclosure. The output of the temperature sensor may be processed by a signal conditioning circuit of the temperature sensor. The processing may include amplification and analog to digital conversion. The processed output of the temperature sensor may be received by the processor (290). In one or more embodiments, the temperature measurements may be used for a temperature compensation of the CO measurement by the CO sensor (230).

The attitude and heading reference system (AHRS) (260) may be used as a backup system for a real-time depiction of the aircraft's attitude. For example, pitch and bank of the aircraft may be displayed in the user interface (310) of the flight application (320) executing on the computing device (300). The AHRS (260) may include sensors for multi-axis attitude sensing. Sensors for roll, pitch, and/or yaw may be used. The sensors may include solid state, microelectromechanical systems (MEMS), gyroscopes, accelerometers, and/or magnetometers. Multiple sensory modalities may be combined using methods for sensor data fusion. The AHRS may be calibrated and re-calibrated to provide accurate AHRS data regardless of the mounting position/orientation of the combined ADS-B and CO detecting device (200). The AHRS (260) may digitally interface with the processor (290) to provide the attitude information.

The status indicators (270) may be used to alert the aircraft crew based on a measured CO concentration inside the aircraft cabin. The status indicators may include visual and/or audio alerts. A light emitting diode (LED) may be used for the visual alert. The LED may change color, based on the measured CO concentration. For example, when the CO concentration is below a threshold, the LED may be green, and when it rises above the threshold it may turn yellow. When the CO level reaches or exceed a potentially dangerous level, the LED may turn red. Multiple LEDs, flashing LEDs, or other types of indicators may alternatively be used to indicate the CO concentration. A buzzer, e.g. a piezoelectric buzzer, may be used for the audio alert. The buzzer may be activated to signal potentially dangerous levels of CO.

The photosensor (280) may be used to detect the ambient light level. The measured ambient light level may be used to adjust the brightness of the visual status indicator(s) (270) to avoid disrupting dark adaptation of the aircraft crew's vision. The photosensor may be a photoresistor, a photodiode, a phototransistor, etc.

The processor (290) may perform multiple functions. The processor (290) may combine the input of the various sensory modalities, e.g., the ADS-B transmissions obtained from the ADS-B module (210) and the CO sensor (220) into a data stream to be sent to the aircraft crew computing devices (190A-190C). The processor may further be configured to monitor CO levels. A description of at least some of the operations performed by the processor (290) is provided below with reference to FIGS. 4A, 4B, and 4C. The processor (290) may be a processor similar to the processor of the computing system described in FIGS. 7A and 7B and may be interfacing with additional hardware components such as the memory (292) and the wireless communication module (294). The processor may be a component of a system on a chip (SOC), i.e. an integrated circuit (IC) that integrates all components of a computing device into a single chip. The SOC may include one or more processor cores, associated memory (e.g., random access memory (RAM), cache memory, flash memory, etc.), a wireless local network (WLAN) interface, input and output devices such as analog to digital converters, etc.

The memory (292) may include volatile and/or non-volatile memory such as random access memory (RAM) and flash memory, respectively. The memory (292) may store instructions for the operations to be performed by the processor (290). In addition, in one or more embodiments, the memory (292) may store a history of received ADS-B transmissions, for example, to support a weather replay at a later time.

The wireless communication module (294) may enable the data stream, including ADS-B and CO sensor data, to be sent to the aircraft crew computing devices (190A-190C). In one embodiment of the disclosure, the wireless communication module (294) is a wireless communication circuitry that operates as an access point supporting simultaneous connection of multiple aircraft crew computing devices (e.g., five aircraft crew computing devices). With the ADS-B and/or CO sensor data being available on multiple aircraft crew computing device, cockpit sharing may be implemented to facilitate workload distribution between the pilot, co-pilot and/or passengers.

The battery (296) may power the components of the combined ADS-B and CO detecting device (200). The battery (296) may be dimensioned to provide power for at least twelve hours. The battery (296) may be a lithium-ion battery or any other type of rechargeable battery.

While FIG. 2 shows a configuration of components, other configurations may be used without departing from the scope of the disclosure. For example, various components may be combined to create a single component. As another example, the functionality performed by a single component may be performed by two or more components. Accordingly, for at least the above-recited reasons, embodiments of the disclosed invention should not be considered limited to the specific arrangements of components and/or elements shown in FIG. 2.

Figure 3:
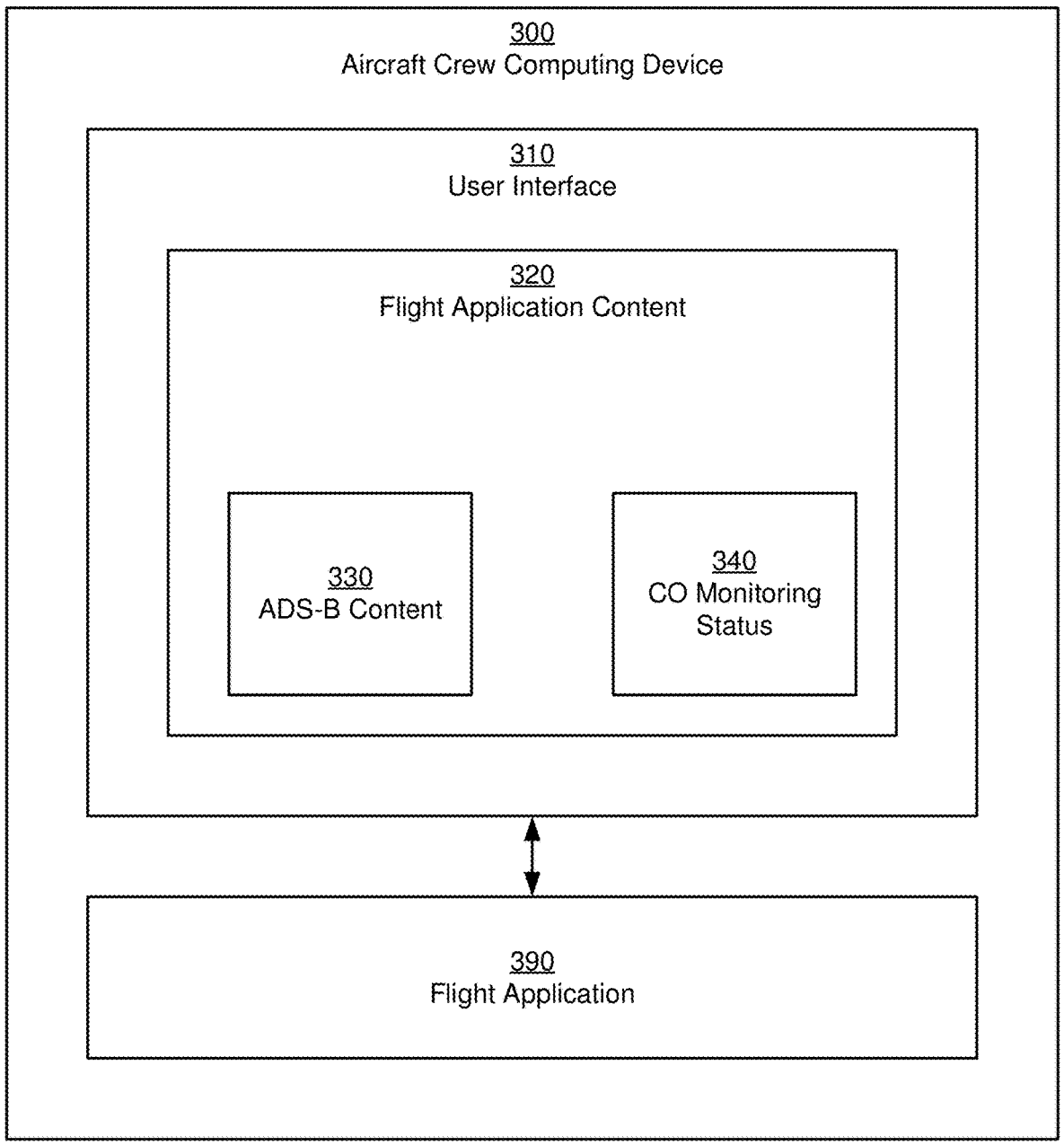
FIG. 3 shows an aircraft crew computing device in accordance with one or more embodiments of the disclosure.

Turning to FIG. 3, an aircraft crew computing device in accordance with one or more embodiments of the disclosure is shown. The aircraft crew computing device (300) may be a portable computing device such as a tablet computer, a laptop or a smartphone. The aircraft crew computing device (300) may include components similar to the computing device shown in FIGS. 7A and 7B. The aircraft computing device may execute a flight application (390) and a user interface (310). The aircraft crew computing device (300), in accordance with one or more embodiments of the disclosure, is configured to execute a set of machine-readable instructions (stored on a computer-readable medium) which, when executed by the aircraft crew computing device (300), perform one or more of the operations described in the flowcharts of FIGS. 5A and 5B.

The flight application (390) may include various components that may serve an aircraft crew, e.g., pilots, co-pilots, etc. These components may include, for example, various types of maps (visual flight rules (VFR) sectionals, VFR and instrument flight rules (IFR) en-route charts, airport diagrams, terminal area charts, world aeronautical charts, surface maps showing terrain features, streets, weather charts, etc.). The maps may be set up as layers and/or overlays that give the flight crew the flexibility to review the most relevant or desired features, while hiding currently non-relevant features in a situation-specific manner. For example, based on an initial zoom level used to show a larger geographic area, only an airport symbol may be shown, and upon zooming in, airport diagrams, complete with runways, taxi labels, and fixed-based operator (FBO) locations may appear.

The flight application may be used to gather and view information during a flight, but also to plan flights and/or to select routes based on flight plans. The selected routes may then be displayed on maps. Maps provided by the flight application may be moving maps for air and/or ground operations that include an own-ship display indicting the current position of the aircraft on the moving map as the flight is progressing.

In one or more embodiments, the flight application (390) obtains information from the combined ADS-B and CO detecting device (200). More specifically, the flight application may rely on data from the ADS-B module (210) to provide the aircraft crew with information such as weather and traffic information. In addition, the flight application (390) may receive data from the CO sensor (220) to notify the aircraft crew in case of a detected increased CO concentration inside the aircraft cabin. In one or more embodiments, the flight application (390) receives a single data stream including packets from both the CO sensor (220) and the ADS-B module (210) and optionally from one or more of the other sensors, such as the temperature sensor, the pressure sensor, etc. One or more operations performed by the flight application (390) may be performed as described below with reference to the flowcharts of FIGS. 5A and 5B.

The user interface (310) may enable an aircraft crew member, e.g., a pilot, co-pilot, or a passenger to interact with the flight application (390). The flight application (390) may provide flight application content (320) to the aircraft crew member, and the flight application (310) may receive input from the aircraft crew member. The flight application content (320) may be provided in a display of the aircraft crew computing device (300). Flight application content (320) may include, but is not limited to, dynamic traffic and/or weather displays for animated next generation radar (NEXRAD), meteorological aerodrome reports (METARs), terminal area forecasts (TAFs), airmen's meteorological information (AIRMETs), significant meteorological information (SIGMETs), pilot reports (PIREPs), textual winds and temps aloft, temporary flight restrictions (TFRs), notices to airmen (NOTAMs), special use airspace (SUA) information, and traffic alerts. At least some of the flight application content (320) may be generated or modified based on input from the combined ADS-B and CO detecting device (200). More specifically, some of the flight application content (320) may be ADS-B content (330) provided by the ADS-B module, and in addition a CO monitoring status (340) may be shown.

The ADS-B content (330) may provide essential, from a flight safety standpoint, additions to the flight application content (320), including weather and traffic information in real-time or near-real time. Additionally, ADS-B content (330) may be "replayed" using ADS-B data stored in the memory (292) of the ADS-B and CO detecting device (200).

The CO monitoring status (340) may include warnings or status messages appearing in the user interface (310) under certain conditions, for example, when a higher-than-normal CO concentration is detected in the cabin. In addition, a CO measurement may always be available, e.g., accessible via a menu.

The flight application content (320) may further be augmented by additional input received from the ADS-B and CO detecting device (200). The flight application content (310) may include a depiction of the aircraft's attitude based on the AHRS (260) of the ADS-B and CO detecting device (200). The aircraft's attitude may be visualized in a synthetic vision system which may be used as a backup glass cockpit. The synthetic vision system may provide pitch and bank, terrain, obstacles, etc., during regular and/or emergency operations. In addition, inflight data, such as ground speed, altitude, estimated time en-route, and/or distance to destination, may be provided.

Similarly, data from the GPS sensor (230) may be used to update maps displayed as flight application content, data from the pressure sensor (240) may be used to provide an altitude estimate, and data from the temperature sensor (250) may be used to display a cockpit ambient temperature.

In addition to the described visual output, audio output may also be provided. For example, certain information such as traffic alerts may be provided in spoken language. To enable an aircraft crew member to receive the audio output, the aircraft crew member may wear a headset with Bluetooth support, paired with the aircraft crew computing device (300).

The user interface (310) may also include input elements that enable the aircraft crew member to control the content provided by the user interface. The input elements may include, but are not limited to a touchscreen interface, a keyboard, and/or a mouse.

Additional functions that relate to the combined ADS-B and CO detecting device may be provided by an aircraft crew computing device. For example, an aircraft crew member may manually activate the buzzer of the combined ADS-B and CO detecting device to familiarize himself or herself with the audio alert issued by the combined ADS-B and CO detecting device when an elevated CO concentration is detected. In addition, an aircraft crew computing device may be used to perform software updates on the combined ADS-B and CO detecting device.

Figure 4A:
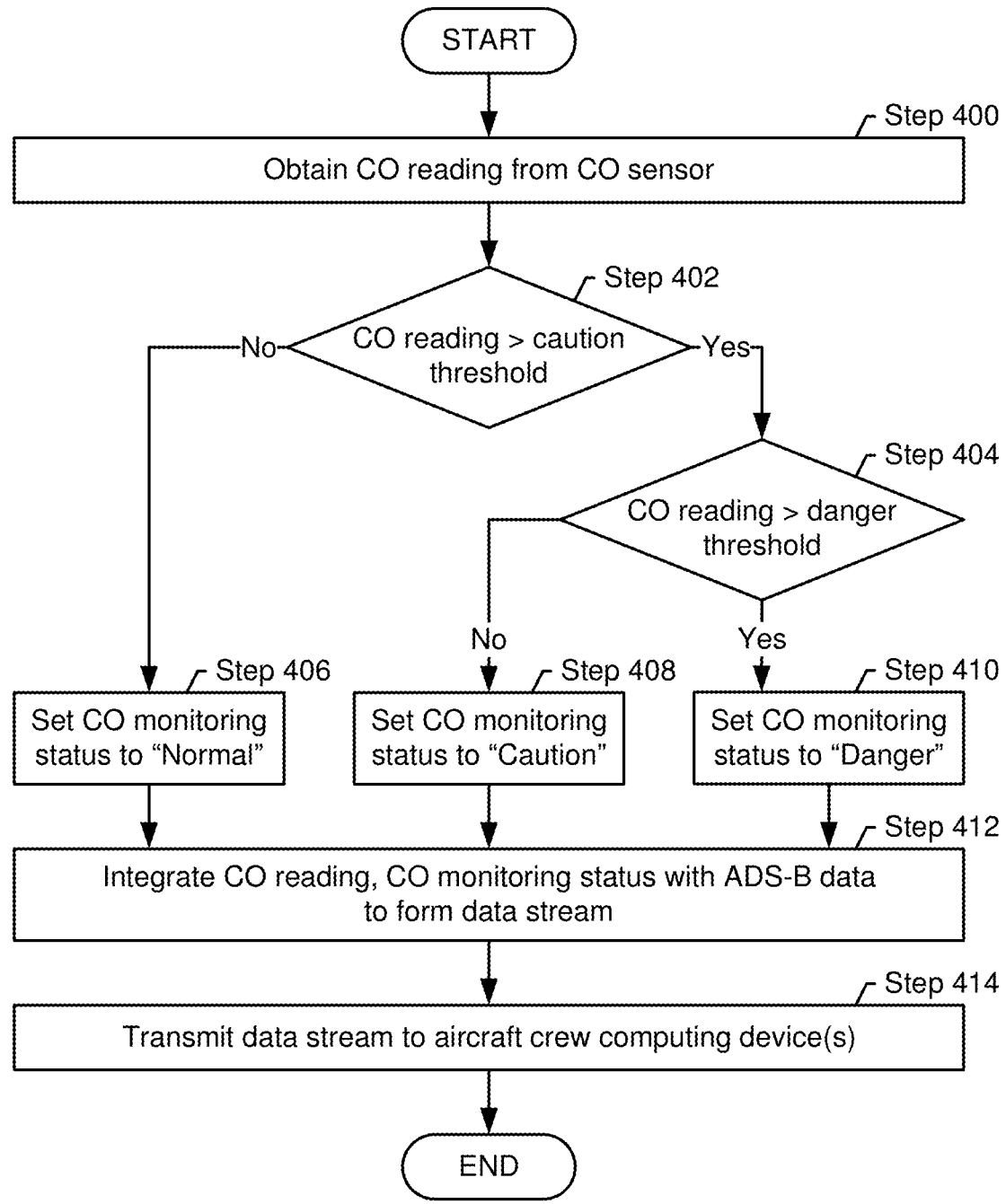
FIGS. 4A, 4B, and 4C show flowcharts describing methods for CO monitoring, performed by the combined ADS-B and CO detecting device, in accordance with one or more embodiments of the disclosure.
Figure 4B:
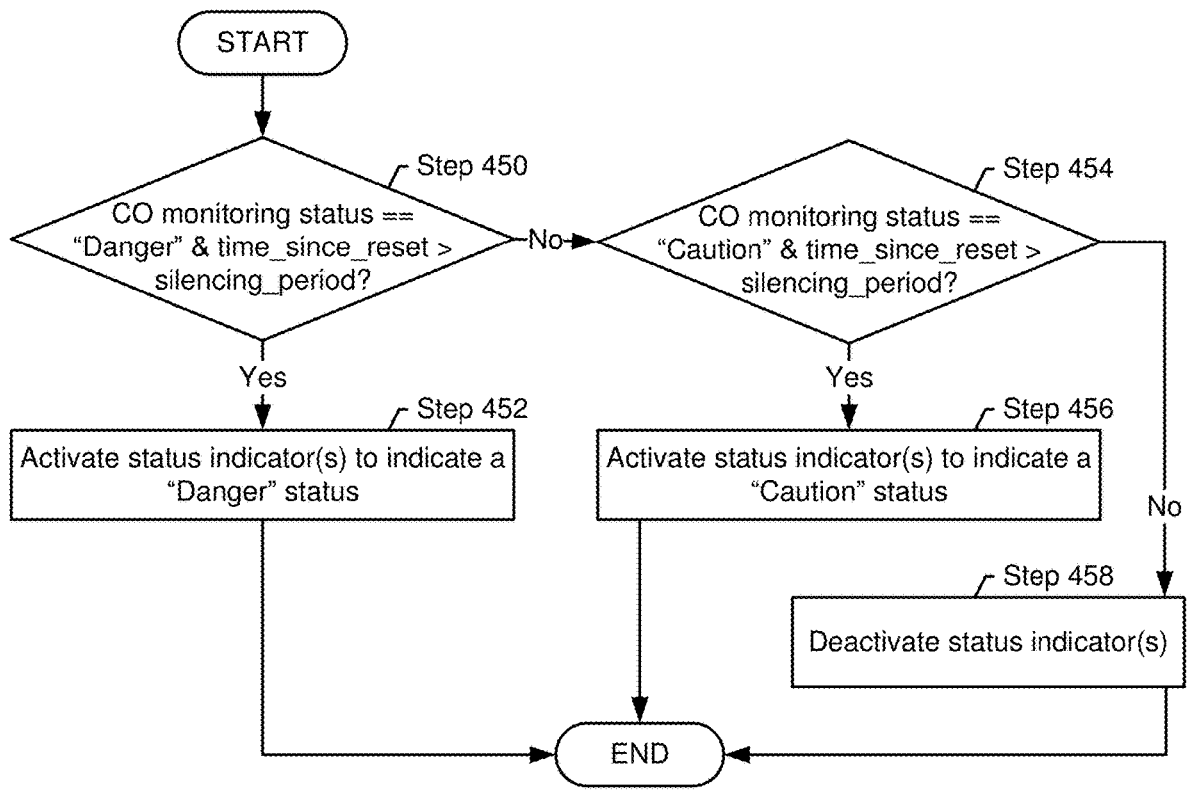
Figure 4C:
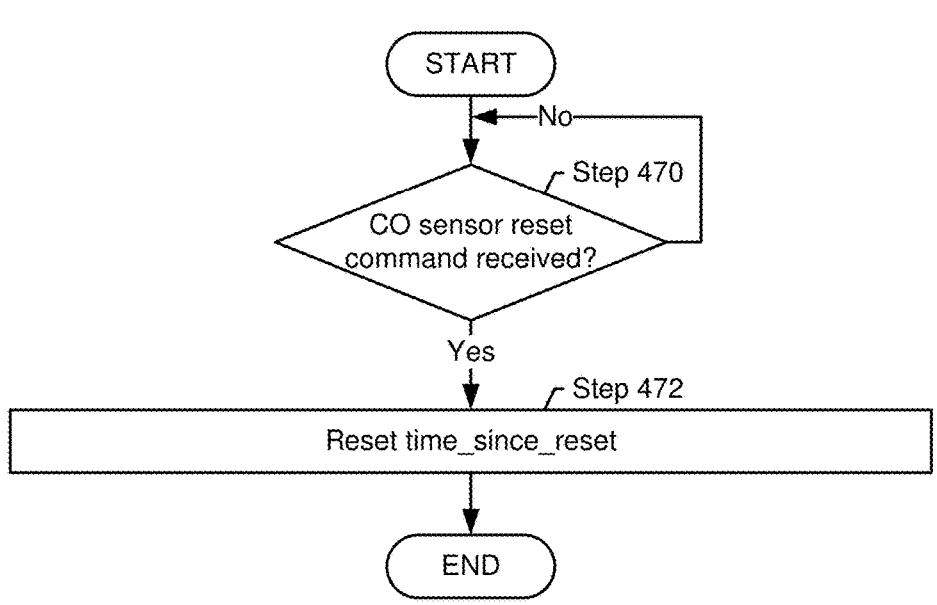
Figure 5A:
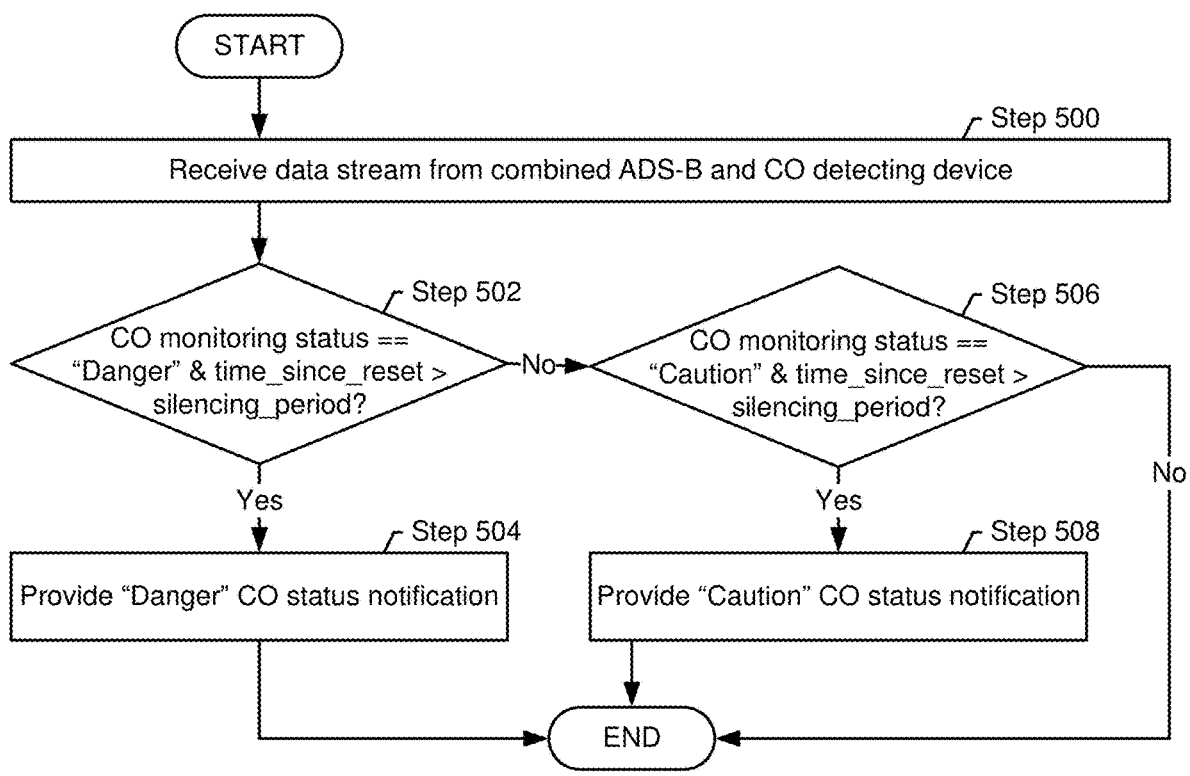
FIG. 5A and FIG. 5B show flowcharts describing methods for CO monitoring, performed by an aircraft crew computing device, in accordance with one or more embodiments of the disclosure.
Figure 5B:
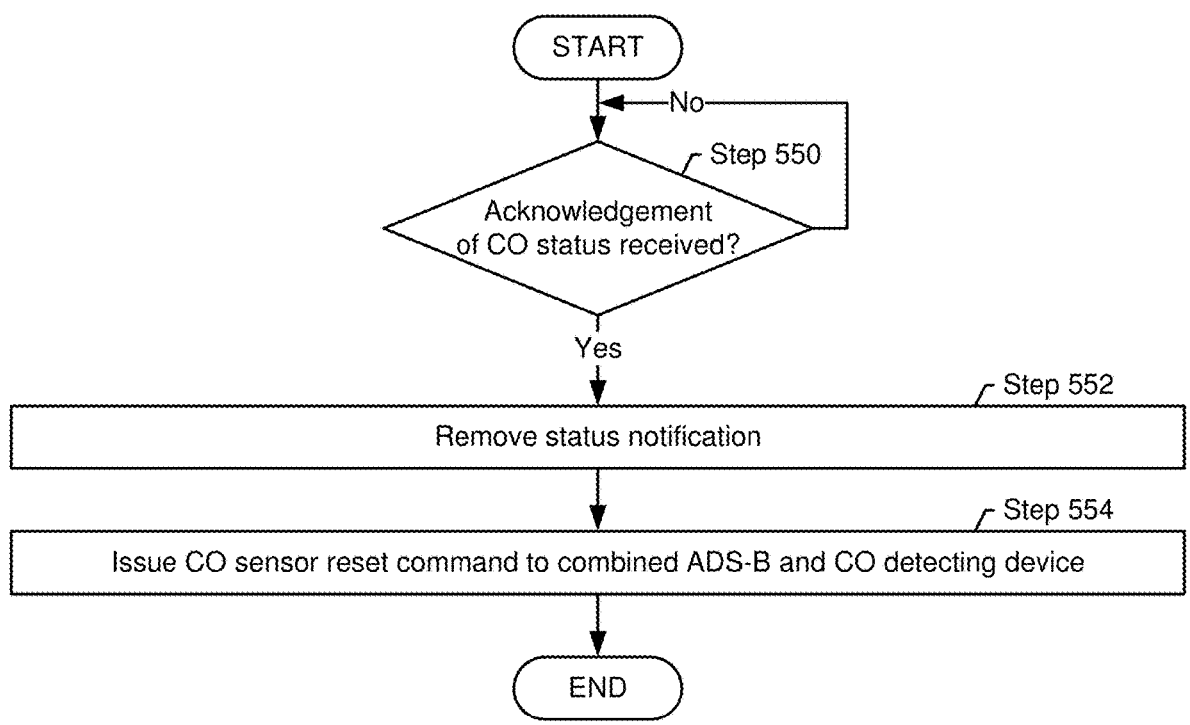

FIGS. 4A, 4B, 4C, 5A, and 5B show flowcharts in accordance with one or more embodiments of the disclosure. While the various steps in these flowcharts are presented and described sequentially, one of ordinary skill will appreciate that some or all of these steps may be executed in different orders, may be combined or omitted, and some or all of the steps may be executed in parallel. In one embodiment of the disclosure, the steps shown in FIGS. 4A, 4B, 4C, 5A, and 5B may be performed in parallel with any other steps shown in FIGS. 4A, 4B, 4C, 5A, and 5B, without departing from the disclosure. The flowcharts of FIGS. 4A, 4B, and 4C show steps that may be performed by a combined ADS-B and CO detecting device, whereas the flowcharts of FIGS. 5A and 5B show steps that may be performed by an aircraft crew computing device.

Turning to FIG. 4A, a method for CO monitoring, performed by the combined ADS-B and CO detecting device, in accordance with one or more embodiments of the disclosure, is shown. The steps of the method may be repeatedly executed to perform a continuous CO monitoring.

In Step 400, a CO reading is obtained from the CO sensor. The CO reading may be obtained by the processor of the combined ADS-B and CO detecting device at regular time intervals.

Subsequently, in Steps 402 and 404, the CO reading is compared against one or more CO threshold values to issue an alert, if the threshold is exceeded.

In Step 402, a test is performed to determine whether the CO reading exceeds a caution threshold. The caution threshold may be set at a particular CO concentration in the ambient air, for example, at 75 parts per million (ppm). Any other value may be selected for the caution threshold, without departing from the disclosure. The caution threshold may be set at a CO concentration known to cause symptoms (e.g., headache, fatigue, nausea) in a human. If the CO reading is at or below the caution threshold, the method may proceed with the execution of Step 406. If the CO reading exceeds the caution threshold, the method may proceed with the execution of Step 404.

In Step 404, a test is performed to determine whether the CO reading exceeds a danger threshold. The danger threshold may be set at a particular CO concentration in the ambient air, for example, at 200 ppm. Any other value may be selected for the caution threshold, without departing from the disclosure. The danger threshold may be set at a CO concentration at which prolonged exposure may cause disorientation, unconsciousness, and/or death. If the CO reading is at or below the caution threshold, the method may proceed with the execution of Step 408. If the CO reading exceeds the caution threshold, the method may proceed with the execution of Step 410.

In Step 406, the CO monitoring status is set to "normal", in Step 408, the CO monitoring status is set to "caution", and in Step 410, the CO monitoring status is set to "danger". The CO monitoring status may be represented by any type of flag or variable.

While not shown, the CO sensor may also provide a CO sensor status. The CO sensor status may be a result of a periodically performed self-test and may indicate whether or not the CO sensor successfully passed the self-test.

In Step 412, the CO reading, the CO monitoring status and/or the CO sensor status are integrated with ADS-B transmission data to form a data stream. The data stream may be based on the GDL90 protocol used for the communications of the between ADS-B device. The protocol may be extended to carry the additional data associated with the CO sensor. In addition, data from the other sensors such as the GPS sensor, the pressure sensor, the temperature sensor, and/or the attitude and heading reference system may be added to the data stream.

In Step 414, the data stream is transmitted to one or more of the aircraft crew devices. The data stream may be transmitted via the wireless communication module. The wireless communication module may operate as a wireless access point, and one or more of the connected aircraft crew computing devices may receive the data stream.

After completion of Step 414, the method may re-execute to continuously provide CO monitoring, and to send updated sensor data to the connected aircraft crew computing device(s).

Turning to FIG. 4B, a method for indicating a CO monitoring status, performed by the combined ADS-B and CO detecting device, in accordance with one or more embodiments of the disclosure, is shown. The steps of the method may be repeatedly executed to provide a recently updated CO monitoring status.

In Step 450, a test is performed to determine whether the CO monitoring status is "danger", and whether a silencing period has expired. Because Step 450 also tests for the expiration of a silencing period, a "danger" CO monitoring status does not result in an alert while in the silencing period. The silencing period may be any time interval, for example, five minutes. Additional details regarding the silencing period are provided below. If the CO monitoring status is "danger" and the silencing period has expired, the method may proceed with the execution of Step 452. Otherwise, the method may proceed with the execution of Step 454.

In Step 452, one or more status indicators of the combined ADS-B and CO detecting device are activated to indicate the "danger" status. The status indicator may be a red LED and/or a buzzer. Any other status indicators may be assigned to the "danger" status without departing from the disclosure.

In Step 454, a test is performed to determine whether the CO monitoring status is "caution". Another test whether the silencing period has expired may or may not be performed. If the CO monitoring status is "caution" and (optionally) if the silencing period has expired, the method may proceed with the execution of Step 456. Otherwise, the method may proceed with the execution of Step 458.

In Step 456, one or more status indicators are activated to indicate the "caution" status. The status indicator may be a yellow LED. Any other status indicators may be assigned to the "caution" status without departing from the disclosure.

While not shown in the flowchart, other status indicators may exist. For example, when a malfunction of the CO sensor is indicated by the CO sensor status, an LED may be flashing.

In Step 458, the one or more status indicators are deactivated. The deactivation may include the silencing of the buzzer. The silenced buzzer may allow an aircraft crew member to assess and potentially address the elevated CO levels without being distracted by the alarm signal of the buzzer. The status indicator LED may nor may not be extinguished in Step 458, depending on the CO monitoring status. Specifically, when the CO level is elevated during the silencing period, the LED may not be extinguished. Accordingly, the LED may indicate a "danger" or "caution" status, even when the buzzer is silenced. Further, the LED, instead of being extinguished at normal CO concentrations, may turn green to indicate that the measured CO concentration is safe.

Turning to FIG. 4C, a method for resetting the CO sensor, in accordance with one or more embodiments of the disclosure, is shown. The steps of the method may be repeatedly executed to enable a reset at any time.

In Step 470, a test is performed to determine whether the CO sensor reset command has been received. The CO sensor reset command may be provided by an aircraft crew member in various ways. The CO sensor reset command may be provided by pressing the power button of the combined ADS-B and CO detecting device. The CO sensor reset command may also be provided via an aircraft crew computing device. For example, an aircraft crew member may confirm a CO status notification provided in the user interface, as further discussed below with reference to FIGS. 5A and 5B. If a CO sensor reset command is detected, the method may proceed with the execution of Step 472. Otherwise, the method may remain in Step 470.

In Step 472, the variable representing the time elapsed since the last reset is re-initialized. In case of an upward-counting timer, the variable may be re-initialized to zero. Alternatively, if a downward-counting timer is used to measure the elapsed time, the downward-counting time may be reset to its initial value, for example, five minutes.

Turning to FIG. 5A, a method for CO monitoring, performed by an aircraft crew computing device, in accordance with one or more embodiments of the disclosure, is shown. The steps of the method may be repeatedly executed to perform a continuous CO monitoring.

In Step 500, the data stream is received from the combined ADS-B and CO detecting device. The data stream may be processed to separate CO sensor-related data from ADS-B data and/or other data. The ADS-B data may subsequently be provided to the flight application and/or the user interface. GPS sensor data, pressure sensor data, temperature sensor data, and/or attitude heading reference system data may be used in a similar manner. The CO sensor data is processed a subsequently discussed.

In Step 502, a test is performed to determine whether the CO monitoring status is "danger", and whether a silencing period has expired. In one embodiment of the disclosure, the CO monitoring status, extracted from the data stream, is used. Alternatively, the CO monitoring status may be determined by comparing the CO reading, extracted from the data stream, against a danger threshold implemented on the aircraft computing device. The threshold may be set as previously described. If the CO monitoring status is "danger" and the silencing period has expired, the method may proceed with the execution of Step 504. Otherwise, the method may proceed with the execution of Step 506.

In Step 504, the "danger" status is signaled. The "danger" status may be signaled by visual and/or acoustic indicators. The visual indicators may include popup windows, status messages, or other visual changes in the user interface that make the aircraft crew member aware of the detected dangerous CO concentration. The audio indicators may include spoken messages, provided to the aircraft crew member, e.g., via the crew member's headset.

In Step 506, a test is performed to determine whether the CO monitoring status is "caution". In one embodiment of the disclosure, the CO monitoring status, extracted from the data stream, is used. Alternatively, the CO monitoring status may be determined by comparing the CO reading, extracted from the data stream, against a danger threshold implemented on the aircraft computing device. The threshold may be set as previously described. Another test whether the silencing period has expired may or may not be performed. If the CO monitoring status is "caution" and (optionally) if the silencing period has expired, the method may proceed with the execution of Step 508. Otherwise, the method may proceed without the execution of Step 508.

In Step 508, the "caution" status is signaled. The "caution" status may be signal by visual and/or acoustic indicators. The visual indicators may include popup windows, status messages, or other visual changes in the user interface that make the aircraft crew member aware of the detected elevated CO concentration. The audio indicators may include spoken messages, provided to the aircraft crew member, e.g., via the crew member's headset.

While not shown in the flowcharts, a CO reading may also be available to the aircraft crew member. The aircraft crew member may access the CO reading in a menu, a status bar, etc. In addition, a message may be provided to the aircraft crew member when the CO sensor fails the self-test.

In one or more embodiments, CO sensor-related messages may be provided to the aircraft crew member regardless of what component of the flight application is currently accessed via the user interface. For example, the user interface may be displaying traffic or weather information when an elevated detected CO reading triggers a popup window to notify the aircraft crew member of the potentially hazardous situation.

Turning to FIG. 5B, a method for issuing a CO sensor reset command, in accordance with one or more embodiments of the disclosure, is shown. The steps of the method may be repeatedly executed to allow an aircraft crew member to reset the CO sensor at any time.

In Step 550, a test is performed to determine whether an acknowledgement of the CO status by an aircraft crew member has been received. An aircraft crew member may provide an acknowledgement in various ways to confirm that he or she is aware of the detected elevated CO concentration. An aircraft crew member may press the power button of the combined ADS-B and CO detecting device. In this case, the combined ADS-B and CO detecting device may notify the connected aircraft crew computing devices of the received aircraft crew member acknowledgement. Alternatively, the aircraft crew member acknowledgement may be received by the aircraft crew computing device itself. For example, an aircraft crew member may confirm a CO status notification provided in the user interface by selecting a checkbox or pushbutton to acknowledge the CO status notification. If an acknowledgement of the CO status is detected, the method may proceed with the execution of Step 552. Otherwise, the method may remain in Step 550.

In Step 552, the CO status notification is canceled. Canceling the CO status notification may involve closing a popup window, silencing an audio message, and/or any other action that restores the user interface to the state prior to the issuance of the CO status notification.

In Step 554, a CO sensor reset command is issued to the combined ADS-B and CO detecting device. The CO sensor reset command may be transmitted using the wireless interface between the ADS-B and CO detecting device and the aircraft crew computing device.

Figure 6:
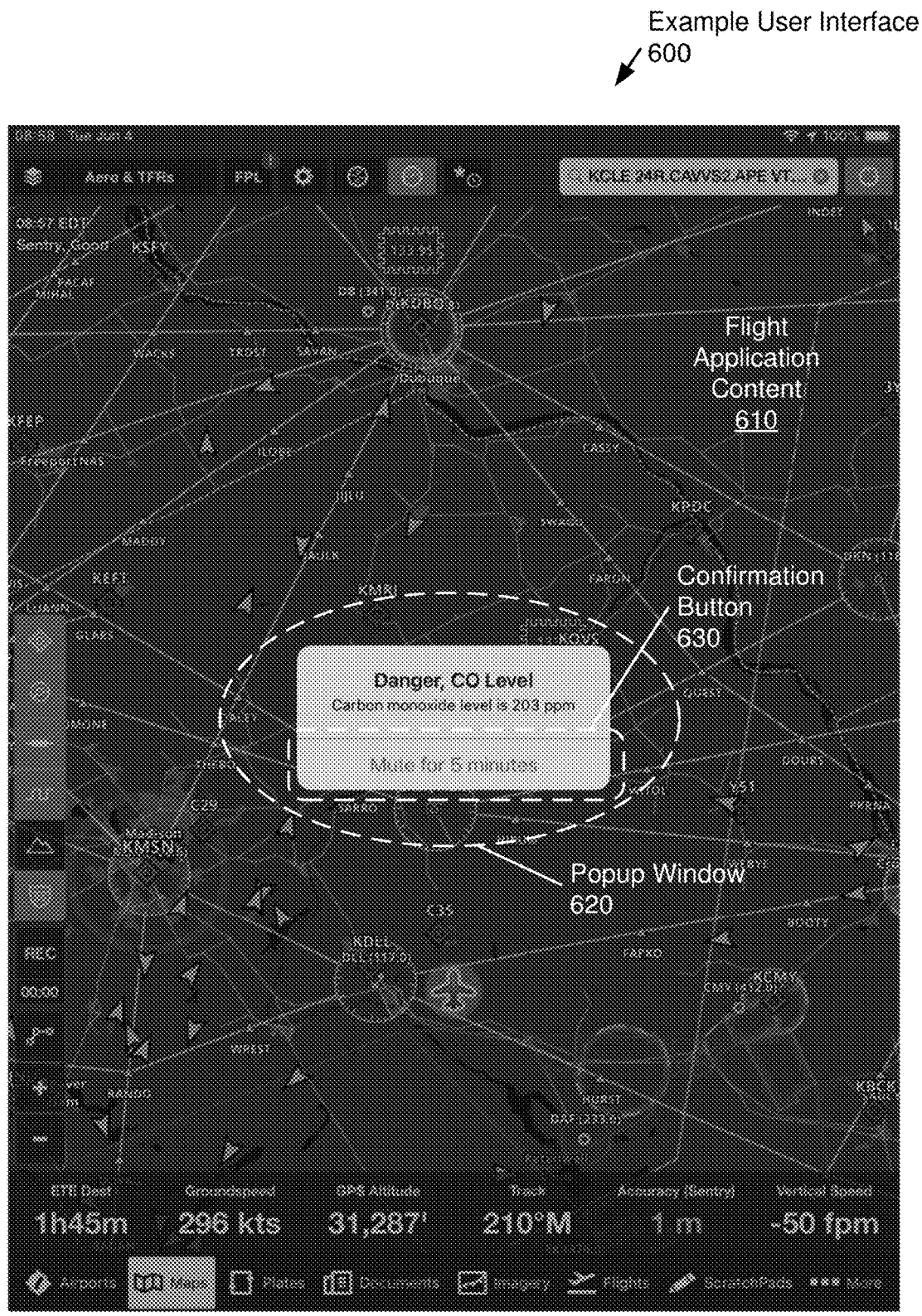
FIG. 6 shows an example of a user interface, in accordance with one or more embodiments of the disclosure.

FIG. 6 shows an example of a user interface (600), in accordance with one or more embodiments of the disclosure. The user interface (600) as shown may be displayed on the aircraft crew computing device (300). The user interface (600) in the example includes flight application content (610). The flight application content (610) is a map as it may be used by an aircraft crew member. A popup window (620) is superimposed. The popup window (620) includes a warning, indicating that the CO level inside the aircraft cabin has reached dangerous levels. The popup window (620) includes a confirmation button (630), allowing the crew member to confirm the warning, which would hide the popup window (620) for five minutes, and which may further silence audio alerts.

Figure 7A:
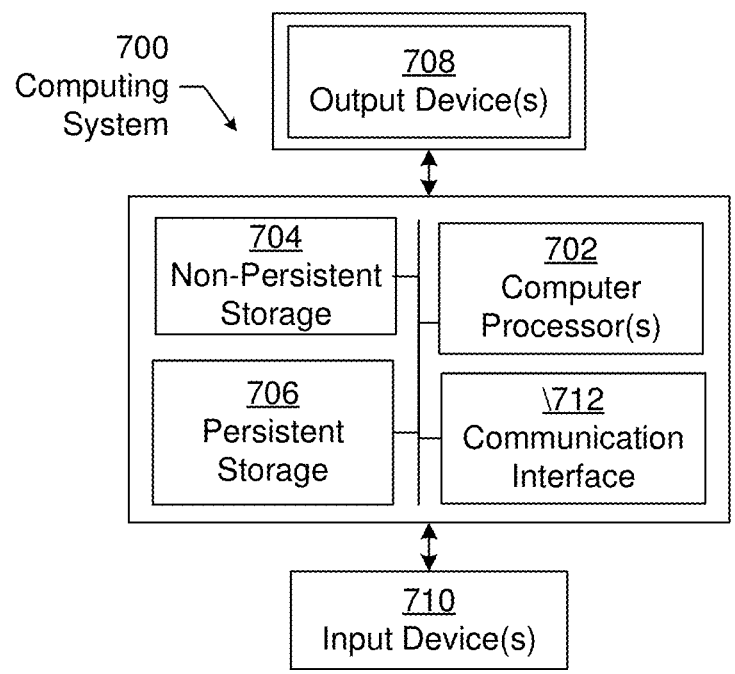
FIGS. 7A and 7B show computing systems in accordance with one or more embodiments of the disclosure.

Embodiments of the disclosure may be implemented on a computing system. Any combination of mobile, desktop, server, router, switch, embedded device, or other types of hardware may be used. For example, as shown in FIG. 7A, the computing system (700) may include one or more computer processors (702), non-persistent storage (704) (e.g., volatile memory, such as random access memory (RAM), cache memory), persistent storage (706) (e.g., a hard disk, an optical drive such as a compact disk (CD) drive or digital versatile disk (DVD) drive, a flash memory, etc.), a communication interface (712) (e.g., Bluetooth interface, infrared interface, network interface, optical interface, etc.), and numerous other elements and functionalities.

The computer processor(s) (702) may be an integrated circuit for processing instructions. For example, the computer processor(s) may be one or more cores or micro-cores of a processor. The computing system (700) may also include one or more input devices (710), such as a touchscreen, keyboard, mouse, microphone, touchpad, electronic pen, or any other type of input device.

The communication interface (712) may include an integrated circuit for connecting the computing system (700) to a network (not shown) (e.g., a local area network (LAN), a wide area network (WAN) such as the Internet, mobile network, or any other type of network) and/or to another device, such as another computing device.

Further, the computing system (700) may include one or more output devices (708), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (702), non-persistent storage (704), and persistent storage (706). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 7B:
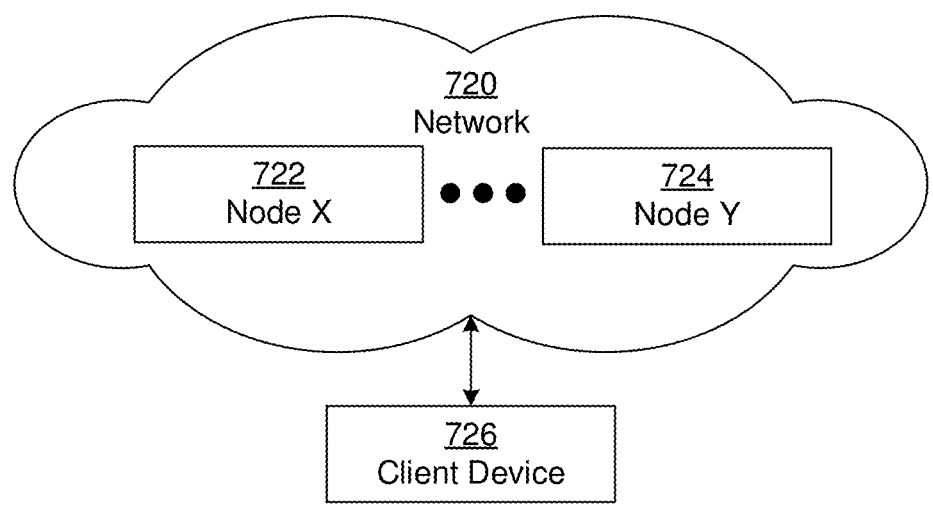

The computing system (700) in FIG. 7A may be connected to or be a part of a network. For example, as shown in FIG. 7B, the network (720) may include multiple nodes (e.g., node X (722), node Y (724)). Each node may correspond to a computing system, such as the computing system shown in FIG. 7A, or a group of nodes combined may correspond to the computing system shown in FIG. 7A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (700) may be located at a remote location and connected to the other elements over a network.

Although not shown in FIG. 7B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (722), node Y (724)) in the network (720) may be configured to provide services for a client device (726). For example, the nodes may be part of a cloud computing system. The nodes may include functionality to receive requests from the client device (726) and transmit responses to the client device (726). The client device (726) may be a computing system, such as the computing system shown in FIG. 7A. Further, the client device (726) may include and/or perform all or a portion of one or more embodiments of the disclosure.

The computing system or group of computing systems described in FIGS. 7A and 7B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system in FIG. 7A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail-such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query provided to a structured data repository (where the data repository may be organized according to a database schema or data format, such as XML).

The extracted data may be used for further processing by the computing system. For example, the computing system of FIG. 7A, while performing one or more embodiments of the disclosure, may perform data comparison. Data comparison may be used to compare two or more data values (e.g., A, B). For example, one or more embodiments may determine whether A>B, A=B, A !=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A–B), and the status flags may be read to determine if the result is positive (i.e., if A>B, then A–B>0). In one or more embodiments, B may be considered a threshold, and A is deemed to satisfy the threshold if A=B or if A>B, as determined using the ALU. In one or more embodiments of the disclosure, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 7A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 7A may include functionality to provide raw and/or processed data, such as results of comparisons and other processing. For example, providing data may be accomplished through various presenting methods. Specifically, data may be provided through a user interface provided by a computing device. The user interface may include a GUI that displays information on a display device, such as a computer monitor or a touchscreen on a handheld computer device. The GUI may include various GUI widgets that organize what data is shown as well as how data is provided to a user. Furthermore, the GUI may provide data directly to the user, e.g., data provided as actual data values through text, or rendered by the computing device into a visual representation of the data, such as through visualizing a data model.

For example, a GUI may first obtain a notification from a software application requesting that a particular data object be provided within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be provided through various audio methods. In particular, data may be rendered into an audio format and provided as sound through one or more speakers operably connected to a computing device.

Data may also be provided to a user through haptic methods. For example, haptic methods may include vibrations or other physical signals generated by the computing system. For example, data may be provided to a user using a vibration generated by a handheld computer device with a predefined duration and intensity of the vibration to communicate the data.

The above description of functions presents only a few examples of functions performed by the computing system of FIG. 7A and the nodes and/or client device in FIG. 7B. Other functions may be performed using one or more embodiments of the disclosure.

While the disclosed technology has been described with respect to a limited number of embodiments, those skilled in the art, having benefit of this disclosed technology, will appreciate that other embodiments can be devised which do not depart from the scope of the disclosed technology as disclosed herein. Accordingly, the scope of the disclosed technology should be limited only by the attached claims.

What is claimed is:

1. An in-flight safety enhancing system comprising:
a combined automatic dependent surveillance broadcast (ADS-B) and carbon monoxide (CO) detecting device configured to receive an ADS-B transmission and obtain a CO reading, wherein the combined ADS-B and CO detecting device comprises a CO sensor configured to perform a periodic self-test; and a flight application executing on an aircraft crew computing device separate from the combined ADS-B and CO detecting device, and configured to:
receive the ADS-B transmission and the CO reading;
augment the flight application with information extracted from the ADS-B transmission; and
provide a CO status notification when the CO reading exceeds a CO threshold value.

2. The in-flight safety enhancing system of claim 1, wherein the CO status notification comprises at least one selected from a visual notification in a user interface configured to display content of the flight application, and an audio notification provided via a headset interfacing with the aircraft crew computing device.

3. The in-flight safety enhancing system of claim 1, wherein the received ADS-B transmission comprises at least one selected from an inflight weather information, a traffic information, and notices to airmen (NOTAMs).

4. The in-flight safety enhancing system of claim 1, further comprising a status indicator configured to provide an alert when the obtained CO reading exceeds a CO threshold value.

5. The in-flight safety enhancing system of claim 4, wherein the CO threshold value establishes a caution threshold for a CO concentration in the ambient air.

6. The in-flight safety enhancing system of claim 4, wherein the CO threshold value establishes a danger threshold for a CO concentration in the ambient air.

7. The in-flight safety enhancing system of claim 4, wherein the status indicator comprises at least one of a light emitting diode and a buzzer.

8. The in-flight safety enhancing system of claim 1, further comprising at least one of a global positioning system (GPS) sensor, a pressure sensor, a temperature sensor, and an attitude and heading reference system (AHRS).

9. The in-flight safety enhancing system of claim 8, wherein the AHRS enables a real-time depiction of the aircraft's attitude on the at least one aircraft crew computing device.

10. The in-flight safety enhancing system of claim 8,
wherein the temperature sensor acquires a temperature reading, and
wherein the processor is further configured to perform a temperature compensation of the CO reading using the temperature reading.

11. A method for enhancing in-flight safety, the method comprising:
obtaining, by a combined ADS-B and CO detecting device, a CO reading from a CO sensor;
receiving, by the combined ADS-B and CO detecting device, an ADS-B transmission; and
integrating, by the combined ADS-B and CO detecting device, the CO reading and the ADS-B transmission into a data stream;
transmitting, by the combined ADS-B and CO detecting device, the data stream to an aircraft crew computing device; and
performing a periodic self-test.

12. The method of claim 11, further comprising:
determining, by the combined ADS-B and CO detecting device, that the CO reading exceeds a CO threshold value, and in response:
providing an alert using at least one status indicator.

13. The method of claim 12, further comprising:
augmenting a flight application executing on the aircraft crew computing device with information extracted from the ADS-B transmission;
presenting the augmented flight application content in a user interface; and
providing, based on the determination that the CO reading exceeds the CO threshold value, a CO status notification in the user interface.

14. The method of claim 13, further comprising:
obtaining, by the aircraft crew computing device, an acknowledgement of the CO status notification by an aircraft crew member operating the aircraft computing device;
providing a CO sensor reset command to the combined ADS-B and CO detecting device; and
silencing the alert of the combined ADS-B and CO detecting device.

15. The method of claim 11, wherein the received ADS-B transmission comprises at least one selected from an inflight weather information, a traffic information, and notices to airmen (NOTAMs).

16. The method of claim 11, further comprising:
providing an alert when the obtained CO reading exceeds a CO threshold value.

17. The method of claim 16, wherein the CO threshold value establishes a caution threshold for a CO concentration in the ambient air.

18. The method of claim 16, wherein the CO threshold value establishes a danger threshold for a CO concentration in the ambient air.

19. An in-flight safety enhancing system comprising:
a combined automatic dependent surveillance broadcast (ADS-B) and carbon monoxide (CO) detecting device configured to receive an ADS-B transmission and obtain a CO reading; and
a flight application executing on an aircraft crew computing device separate from the combined ADS-B and CO detecting device, and configured to:
receive the ADS-B transmission and the CO reading;
augment the flight application with information extracted from the ADS-B transmission;
provide a CO status notification when the CO reading exceeds a CO threshold value; and
a temperature sensor, wherein:
the temperature sensor acquires a temperature reading, and
the processor is further configured to perform a temperature compensation of the CO reading using the temperature reading.

20. The in-flight safety enhancing system of claim 19, wherein the combined ADS-B and CO detecting device comprises a CO sensor configured to perform a periodic self-test.

* * * * *